United States Patent [19]

Puchy

[11] Patent Number: 4,753,237
[45] Date of Patent: Jun. 28, 1988

[54] BOW SPRING RETRACTOR DEVICE

[76] Inventor: David P. Puchy, P.O. Box 382, Epping, N.S.W. 2121, Australia

[21] Appl. No.: 860,107

[22] Filed: May 6, 1986

[30] Foreign Application Priority Data

May 6, 1985 [AU] Australia ............................ PH0445

[51] Int. Cl.⁴ ..................... A61B 17/08; A61B 1/32; A61B 17/02
[52] U.S. Cl. ................... 128/335; 128/17; 128/20; 128/334 R
[58] Field of Search ............... 128/335, 333.5, 334 R, 128/20, 18, 17, 19

[56] References Cited

U.S. PATENT DOCUMENTS

| | | | |
|---|---|---|---|
| 569,839 | 10/1896 | Roeloffs | 128/17 |
| 4,344,420 | 8/1982 | Forder | 128/20 |
| 4,412,532 | 11/1983 | Anthony | 128/20 |

OTHER PUBLICATIONS

*Universal Retractor for Cavitary Surgery*, Biomedical Engo, (U.S.A.), vol. 8, No. 5, Sep.-Oct. 1974.

Primary Examiner—Richard C. Pinkham
Assistant Examiner—Gary Jackson
Attorney, Agent, or Firm—Hopgood, Calimafde, Kalil, Blaustein & Judlowe

[57] ABSTRACT

A retractor device to facilitate aligning and opposing the edges of a wound preparatory to its closing. The retractor is a resiliently flexible strip member having hooks attached at each end thereof. The hooks are adapted to engage the extremities of the incision when the strip member is bent to a partially bowed configuration so that the resulting tension which is applied through the hooks operates to align the edges of the wound along the entire length of the incision.

11 Claims, 3 Drawing Sheets

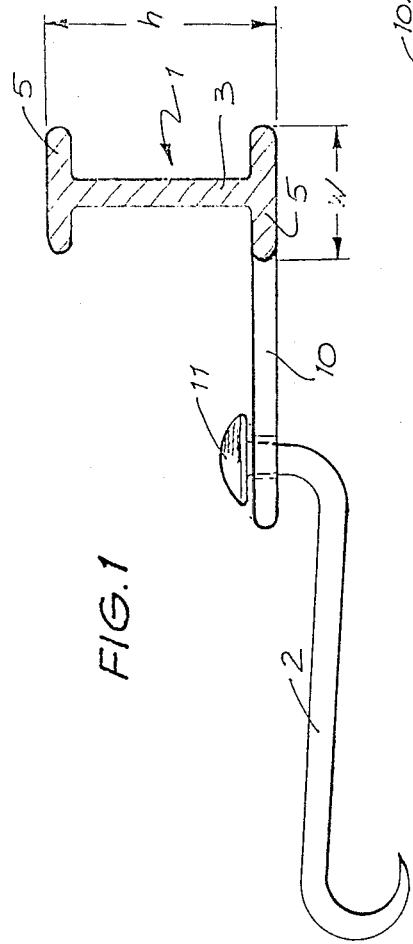
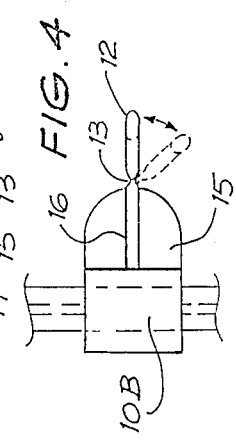
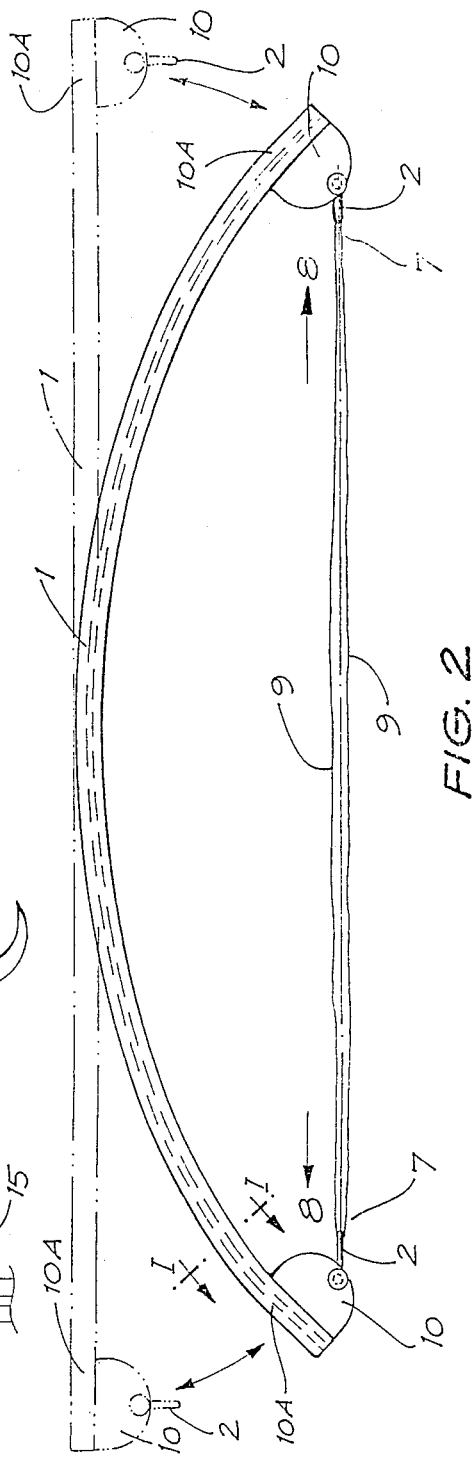

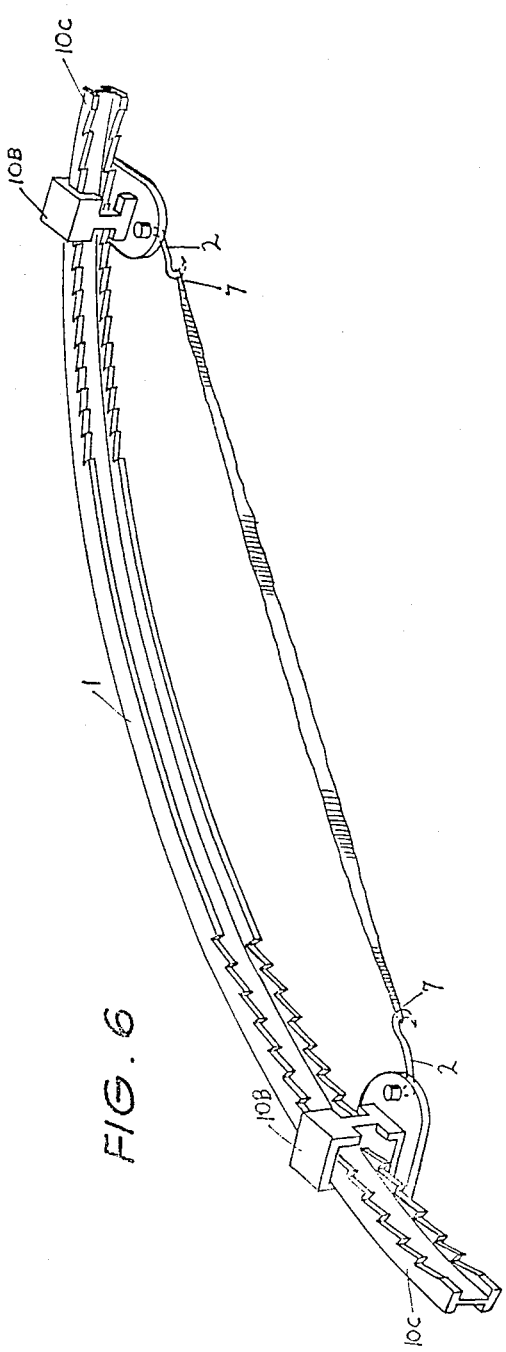
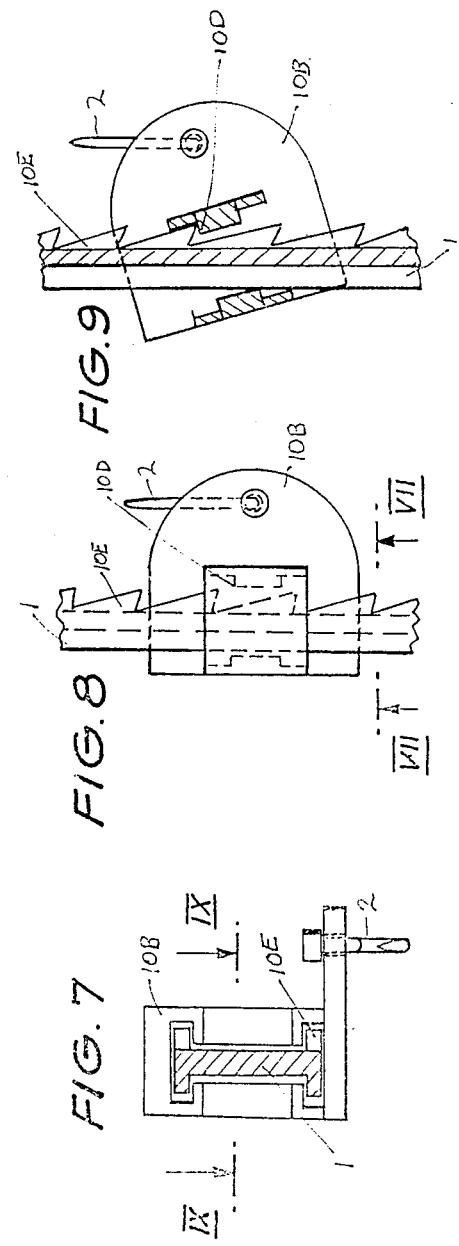

BOW SPRING RETRACTOR DEVICE

This invention relates to improvements in surgical instruments and more particularly discloses a retractor device to facilitate aligning and apposing the edges of a wound preparatory to its closing.

Presently the most common procedural methods used for closing incision or trauma wounds are with thread sutures and stainless steel staples, and to a lesser degree, stainless steel clips, adhesive tapes and zipper apparatus. Irrespective of the closing means, it is essential in each instance to properly align and appose the wound edges. This ensures that healing occurs as quickly as possible and without avoidable complications such as subcutaneous infections which may result either directly or indirectly from poor apposition.

Short wounds requiring only a few sutures or staples are usually approximated by the surgeon with his fingers. However longer wounds are more commonly approximated with the aid of instruments such as skin hooks or forceps. It is common practice to insert a first skin hook in one end of the incision and a second skin hook in the opposite end of the said incision, align them along the axis of the said incision and draw them apart to tension the tissue along both edges. This aligns and accurately apposes the edges of the incision preparatory to closing.

Such procedure however, has the disadvantage of requiring an assistant to manipulate and tension the skin hooks. The magnitude of the applied tensioning force must also be precisely and constantly monitored during the suturing or stapling operation, so that the apposed faces are closed evenly along the length of the incision. In this way healing is aided and the formation of resulting scar tissue is both minimised and constant, for better cosmetic results.

It is therefore an object of this invention to ameliorate the aforementioned disadvantages and accordingly this invention discloses a retractor device to facilitate approximation of the wound prior to closing. Said retractor device comprising a resiliently flexible strip member with hook means attached substantially at each end thereof, which are adapted to engage the extremities of the incision when the said strip member is bent to at least a partially bowed configuration so that the resulting tension which is applied through the hook means operates to align and appose the edges of the wound along the entire length of the said incision.

The flexible strip member of the said retractor device may be manufactured in several varying lengths to better accommodate different incision lengths and to provide a choice for the degree of skin tensioning required to suit individual wounds. The hook attachment means may be permanently united to the said flexible strip member substantially at each end thereof or alternatively, said hook attachment means may be slidably adjustable along the length of the said flexible strip member.

The said hook means may be integrally affixed (i.e. moulded) to the said hook attachment means in such a way as to facilitate hinging of the hook means relative to the hook attachment means or alternatively, said hook means may be formed individually from stainless steel and pivotally mounted in the said hook attachment means.

A preferred embodiment of this invention will now be described with reference to the attached drawings in which:

FIG. 1 illustrates a sectional end elevation of a retractor in an "unstrung" position showing hook attachment means permanently united;

FIG. 2 illustrates a plan view of the apparatus of FIG. 1 in "unstrung" (chain dotted lines) and a "strung" position over a wound;

FIG. 3 illustrates a sectional view and end elevation of a retractor in an "unstrung" position, showing a slidably adjustable hook attachment means having an integrally mounted hinged hook means.

FIG. 4 illustrates a plan view of the apparatus of FIG. 3;

FIG. 6 illustrates use of a retractor of a second embodiment of the present invention;

FIG. 7 illustrates sectional and elevation of apparatus of FIG. 6 showing hook attachment means;

FIG. 8 illustrates a plan view of the apparatus of FIG. 7; and

FIG. 9 illustrates operation of the apparatus of FIG. 7 and 8.

Figure 5:
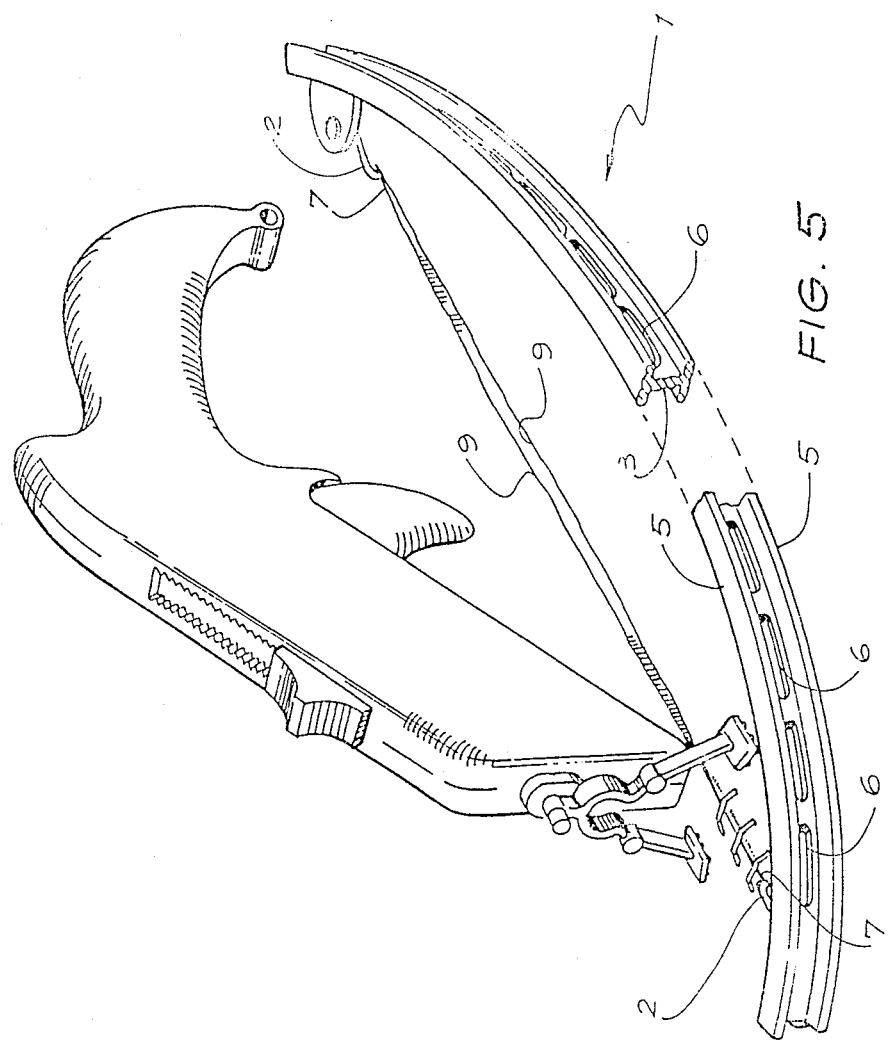
FIG. 5 illustrates use of the retractor of FIGS. 1 and 2, in co-operation with a stapling instrument.

Referring now to FIGS. 1 and 2 the device comprises a flexible strip 1 with hooks 2 disposed substantially at each end thereof. The preferred cross-sectional configuration of the said strip is best shown in FIG. 1 and comprises a central web 3 located between flanges 5. The web may be constructed with spaced apart cut outs 6 to save material and improve flexibility. Also to improve the stability of the strip 1 when bowed, the cross-sectional height "h" normal to the plane of bending is greater than the width "w".

The device is adapted to lie flat against a patient's body with the hooks 2 offset below the lower edge of the strip 1 so as to readily engage the extremities 7 of a surgical incision as illustrated in FIG. 2. The resiliency of the strip 1 when bowed as shown, applies a constant tensioning force to the wound in the direction of arrows 8. This in turn tensions the tissue along the length of the edges 9 of the incision so that the said edges are simultaneously aligned and apposed prior to closing with staples or sutures.

With this particular embodiment, the hook attachment means 10A located substantially at each end of the strip 1, are formed as semi-circular pads 10 which provide stable bearing surfaces against the patient's skin. The hooks 2 are preferably pivotally mounted in the pads 10 as illustrated in FIG. 1 whereby they self align under the tension of the bowed strip when inserted in the wound extremities 7. The pads 10 locate the hooks 2 in a position offset from the centre line of the flexible strip 1. This provides the advantage of giving a unobstructed access to the incision 9 for closing purposes.

A wide variety of other arrangements may be used both in reference to the cross sectional shape of the flexible strip 1 and to the hook means 2 and hook attachment means 10A. One example of this is the slidably adjustable hook attachment means 10B shown in FIGS. 3 and 4 whereby the hook means 12 and stiffening web 16 are integrally moulded with the said hook attachment means and is wasted at the neck 13 to form a hinge in a plane perpendicular to the base 14 of the pad 15. It will be apparent from the foregoing that the hook means 2 shown in FIG. 1 could be substituted for the above described hook means shown in FIGS. 3 and 4.

The purpose of providing slidably adjustable hook attachment means 10B is that it enables fewer varying lengths of the flexible strip 1 to be utilised to accommodate all incision lengths and simultaneously gives the surgeon more flexibility to select the desired bow tension best suited to the individual wound to be approximated and closed.

When slidably adjustable hook attachment means 10B are utilised, a series of location means on the flexible strip 1 can be incorporated there on for the purpose of locating the sliding hook attachment means 10B. The location means can be in the form of a releasable ratchet type mechanism which allows selective movement upon activation.

Illustrated in FIGS. 6 to 9 in another embodiment of the present invention which comprises a flexible strip 1 and slidably adjustable hook attachment means 10B, similar to that of FIGS. 3 and 4. Hook attachment means 10B is illustrated in detail in FIGS. 7 to 9. The flexible strip 1 includes toothed ends 10C which are adapted to engages shoulders 10D on hook attachment means 10B. Shoulders 10D will only engage teeth 10E when hook attachment means 10B are rotated relative to flexible strip 1. This will occur when the flexible strip 1 is in at least a partially bowed configuration, with the hooks 2 in position in wound extremities 7.

Additionally, though the cross-section of the flexible strip 1 is generally constant along its length, it is envisaged that on devices with permanently fixed hook attachments as shown in FIG. 2 the width of the flanges 5 could be reduced by way of tapering towards each extremity. This would provide increased flexibility towards the extremities of the strip and avoid concentrating the stresses in its mid region when the said strip was in a bowed position.

From the aforegoing it will be appreciated that this invention provides a novel, unique and extremely useful surgical instrument that facilitates both accurate apposition of wounds preparatory to closing, and one man closing procedures. The particular embodiments described in the foregoing text are not meant to restrict this invention and a wide variety of modifications may be made which would be apparent to anyone skilled in the art. For example, having one permanently fixed hook attachment means substantially at one end of the flexible strip and a slidably adjustable hook attachment means located towards the opposite end of the said strip. Also it is to be understood that the invention is not limited to any particular length or lengths for the flexible strip, or to any particular size for the "h" and "w" relationship illustrated in FIG. 1. Indeed it is envisaged that the strip could even be constructed in a telescoping or segmented manner to enable its adjustment to any desired length. It is further envisaged that both reusable and disposable models of this device could be cheaply manufactured from appropriate materials.

The claims defining the invention are as follows, I claim:

1. A device for approximating the margins of an incision, said device comprising:
    a resiliently flexible strip adapted for bending between a rest position when said strip is in a linear configuration and a work position when said strip is in a bowed configuration;
    a plurality of hook attachment means mounted on said strip and adapted to pivotally support a hook, at least one of said hook attachments means being selectably positionable along said strip,
    and slender hook means attached to each of said attachment means adapted to engage the extremities of an incision when said strip is in said bowed configuration,
    wherein, when the margins of an incision are to be drawn together preparatory to implanting staples or sutures to secure said incision closed, said hook means are placed in an opposing manner at said extremities of said incision when said resilient strip is manually bent in a bowed configuration suitable for the length of said incision, said strip in said bowed configuration thereby applying tension to said incision when said strip is released and thereby axially aligning and tensioning the tissue of said incision and drawing the margins of a wound together.

2. A device according to claim 1, wherein the said hook means are disposed eccentric to the longitudinal axis of said flexible strip.

3. A device according to claim 2, wherein the cross sectional height of the said strip normal to the plane of bending is greater than the width of said strip.

4. A device acording to claim 3, wherein said hook attachment means provide bearing surfaces which bear against the extremities of the incision.

5. A device according to claim 4, wherein at least one selectably positionable hook attachment means is provided with releasable latching means for locating said hook attachment in selected position along said strip.

6. A device according to claim 5, wherein said releasable latching means comprises interengagement between a bearing surface on said at least one selectably positionable hook attachment means and at least one tooth of a series of teeth formed on said strip.

7. A device according to claim 6, wherein bowing of said strip causes a canting of said selectably positionable hook attachment means relative to the longitudinal axis of said strip to thereby engage and hold said selectably positionable hook attachment means in locking engagement with said at least one tooth when said hook means are engaged in opposing extremities of a wound or incision.

8. A device according to claim 7, wherein means are provided for adjustment of the said axial tension on said wound or incision whilst said strip is in engagement with said wound or incision.

9. A device according to claim 8, wherein the said tension adjustment is effected by a manual realignment of said at least one selectably positionable hook attachment means to a perpendicular relationship to the longitudinal axis of said strip thereby enabling manual movement of and increased or reduced bowing of said strip relative to said realigned hook means.

10. A device according to claim 9, wherein the flexible strip is of variable cross section along its length.

11. A device according to claim 10, wherein the said strip is located in position by the engagement of the hook attachment means and in contact with the body tissue at the extremities of said incision.

* * * * *